United States Patent [19]
Krabetz et al.

[11] Patent Number: 5,087,744
[45] Date of Patent: Feb. 11, 1992

[54] PREPARATION OF METHACRYLIC ACID

[75] Inventors: Richard Krabetz, Kirchheim; Gerd Duembgen, Ludwigshafen; Franz Merger, Frankenthal; Michael Jaeger, Schifferstadt; Fritz Thiessen; Herbert Vogal, both of Ludwigshafen, all of Fed. Rep. of Germany

[73] Assignee: BASF Aktiengesellschaft, Ludwigshafen, Fed. Rep. of Germany

[21] Appl. No.: 213,837

[22] Filed: Jun. 30, 1988

[30] Foreign Application Priority Data

Jul. 2, 1987 [DE] Fed. Rep. of Germany ....... 3721865

[51] Int. Cl.$^5$ .................. C07C 51/25; C07C 57/055
[52] U.S. Cl. ................................ 562/535; 562/600
[58] Field of Search .................. 562/535, 534, 600

[56] References Cited

U.S. PATENT DOCUMENTS 4,558,028 12/1985 Tsuneki et al. ................. 562/535
4,985,592 1/1991 Ishii et al. ..................... 562/534

FOREIGN PATENT DOCUMENTS 0194620 9/1986 European Pat. Off. .
2041930 9/1980 United Kingdom .
2045759 11/1980 United Kingdom .
2116963 10/1983 United Kingdom .

Primary Examiner—Jose G. Dees
Attorney, Agent, or Firm—Oblon, Spivak, & Neustadt

[57] ABSTRACT

Methacrylic acid can be prepared with advantage by gas phase oxidation of methacrolein or isobutyraldehyde over Mo- and P-containing catalysts at from 250° to 400° C. with cooling of the hot reaction gas to below 100° C., absorption of the methacrylic acid in a water-operated absorption column, at below 100° C. and partial recycling into the oxidation reactor after admixture of methacrolein or isobutyraldehyde and oxygen by feeding a quantity of methacrolein or isobutyraldehyde equal to the quantity of methacrolein or isobutyraldehyde consumed in the reaction in liquid form together with a polymerization inhibitor into the reactor gas in the lower two-thirds of the absorber column and upstream of the feed point for the fresh methacrolein or isobutyraldehyde or down-stream of the absorption column splitting off the reactor off-gas a side stream which is washed in a wash column operated with water at <10° C. to remove unconverted methacrolein or isobutyraldehyde which is fed as an aqueous solution to the top of the absorption column.

6 Claims, 2 Drawing Sheets

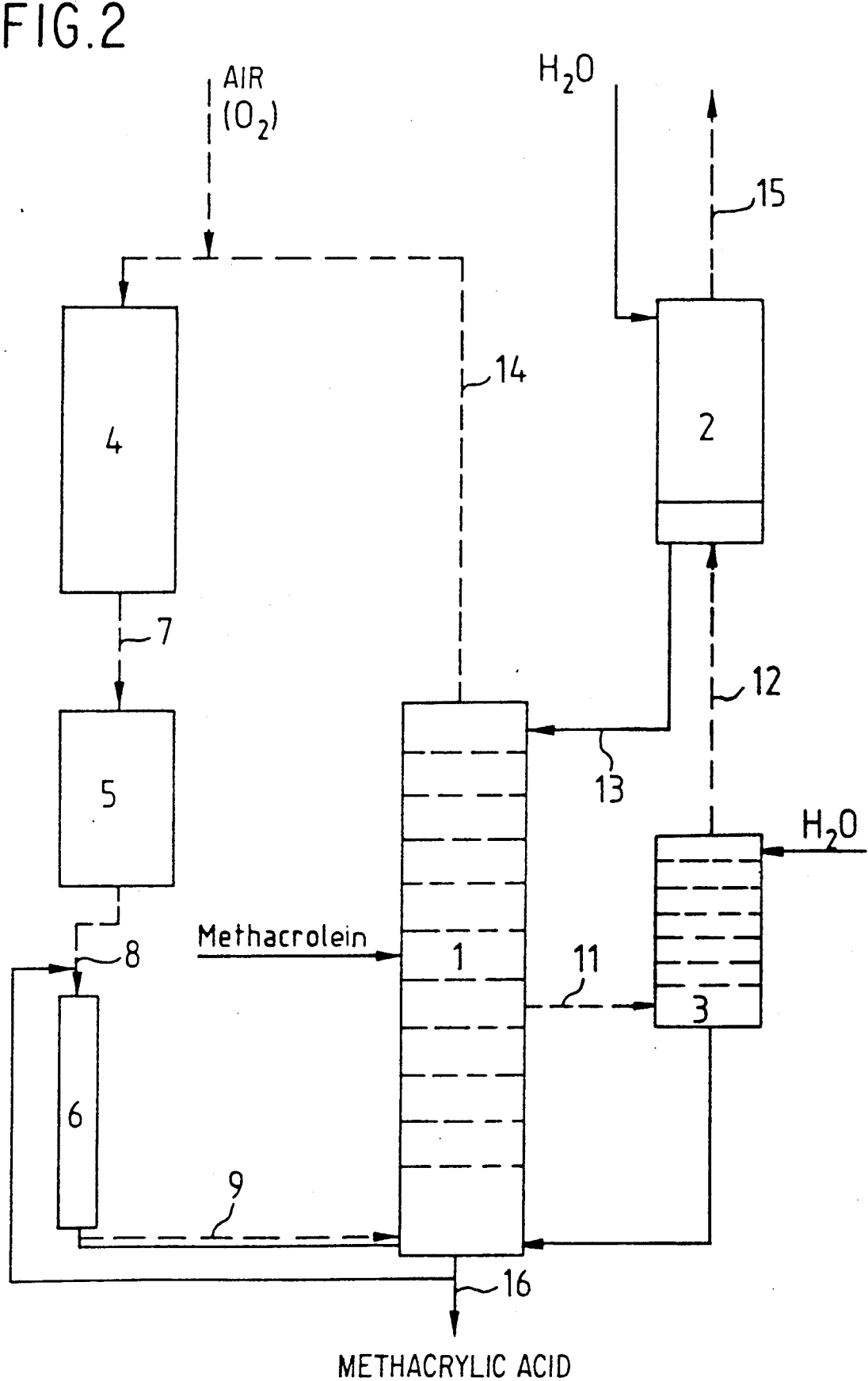

PREPARATION OF METHACRYLIC ACID

BACKGROUND OF THE INVENTION

It is known to prepare methacrylic acid by gas phase oxidation of methacrolein or isobutyraldehyde with oxygen- and steam-containing gas mixtures over molybdenum- and phosphorus-containing catalysts.

Most of the existing processes for preparing methacrylic acid start from methacrolein obtained by catalytic oxidation of isobutylene or tertiary butanol. In the first-second connected process, the reaction gas of the primary oxidation stage where isobutylene or tertiary butanol was converted into methacrolein is fed directly, without isolation of the methacrolein formed, into the secondary oxidation stage where the methacrolein is oxidized to methacrylic acid over Mo- and P-containing heteropolyacids. In the alternative first-second separated process, the methacrolein produced in the primary oxidation stage is separated from the reaction gas, is mixed with $O_2$ or air, steam and an inert gas and is then fed to the secondary oxidation stage. Other processes start from isobutyraldehyde or from methacrolein obtained by condensation of propanal and formaldehyde in the presence of secondary amines or animals as catalysts. The problem with all the processes mentioned is that (a) the formation of methacrolein in the primary stages is by the very nature of the reaction accompanied by the formation of high-boiling byproducts which reduce the activity and selectivity of the catalysts of the secondary oxidation stage and by being precipitated in a finely divided form cause an increase in the pressure drop; and (b) the existing catalysts for the oxidation of methacrolein do not give complete conversion of the methacrolein in the secondary oxidation stage, so that unconverted methacrolein needs to be isolated for economic reasons and recycled into the oxidation stage. The strong tendency of the product mixture obtained in the secondary oxidation stage, containing methacrolein and unsaturated high boilers, to polymerize and to form difficult-to-remove aerosols easily leads to solid deposits in the downstream cooling zones and heat exchangers and hence to an increase in the pressure losses, frequently after short operating periods. In addition, the high boilers can pass as aerosols together with the recycled methacrolein-containing gas streams into the oxidation stage, there to initiate the difficulties mentioned under (a).

Various solutions to these problems have been proposed, but they are not satisfactory and in general are only directed to the two-stage processes based on isobutylene/tertiary butanol.

For the first-second connected process it is proposed for example in U.S. Pat. No. 4,558,028 to use low pressure drop hollow cylinders of defined composition as catalysts in the methacrolein oxidation stage in order to moderate the adverse consequences of the deposition of high-boiling byproducts, such as terephthalic acid and tarlike mixtures. However, this measure does not constitute a fundamental solution to the overall problem, since the adsorption or deposition on the catalyst is not prevented. To suppress the deposition of polymer in the critical cooling zones downstream of the secondary oxidation stage and the blowthrough of aerosols, GB Patent 2,116,963 proposes for the same process that the cooled reaction gas emerging from the oxidation reactor at 250° C. be rapidly cooled down to about 50° C. with an aqueous methacrylic acid solution in a cooling tower equipped with perforated plates without downcomers and that the offgas leaving the cooling zone in the form of an aerosol be washed in a Venturi washer at about 40° C. with an aqueous methacrylic acid solution before being fed into a methacrylic acid absorber. A portion of the methacrolein-containing offgas from the absorber is reacted in a third oxidation reactor, while the remaining portion of the offgas is washed in a water-operated absorber at from 10° to 15° C. to remove the methacrolein. All in all, the process of GB Patent 2,116,963 demands a great deal in terms of apparatus and is associated with losses of useful product of not less than 1 mol %.

In the typical first-second separated processes of GB Patents 2,041,930 and 2,045,759, the methacrolein produced from isobutylene in the primary oxidation stage is washed together with the bulk of the organic byproducts out of the reaction gas in two absorption stages, then in GB Patent 2,041,930 charged as an aqueous solution onto the upper end of a stripping column and driven out there with cycle gas from the secondary oxidation stage at base of column temperatures of 120° C. The cycle gas is charged with methacrolein and water vapor is passed direct to the oxidation reactor. In this process too it cannot be ruled out that high-boiling byproducts having a catalyst-poisoning action pass into the second oxidation stage, since the aqueous methacrolein solution is introduced at the upper end of the stripping column. The reaction gas from the secondary oxidation reactor is, according to British Patent 2,045,759 GB, passed direct or after indirect cooling to 150° C. into a cooling tower and is quenched there with a recycled stream of liquid to about 40° C., while the cooling tower offgas, which contains methacrolein, water and byproducts, is recycled into the oxidation stage. According to GB Patent 2,116,963, the measures of GB Patent 2,045,759 are not suitable for preventing the deposition of polymeric solids in the cooling zones and the formation of aerosols and/or their passing into the oxidation reactor.

EP Patent Application 194,620 describes a process for preparing methacrylic acid by gas phase oxidation of methacrolein which has been obtained by reacting propanal with formaldehyde and which contains interfering and/or high-boiling byproducts comprising inter alia 2-methylpentenal, dimeric methacrolein, 2-methylpentanal, 3-methoxyisobutyraldehyde as well as from 0.5 to 3% by weight of water and small amounts of methanol, formaldehyde and propionaldehyde. A recommendation is to purify the methacrolein before introduction to the oxidation reactor by absorption or distillation in such a way that the concentration of oxygen-containing and/or unsaturated compounds having more than 4 carbon atoms in the gas mixture is less than 0.2% by weight, based on the methacrolein. Otherwise this European patent application reveals no measures for preventing solid deposits in the critical cooling zones and aerosol formation in the isolation of methacrylic acid and of unconverted methacrolein which go beyond the above-discussed proposals.

In the course of further work on the last process it was found that prepurification of the methacrolein by the method of EP Patent Application 194,620 is not completely sufficient to prevent, in sustained industrial operation, temporary or irreversible poisoning of the oxidation catalysts by impurities in the methacrolein on using the prior art measures for isolating the methacrylic acid and the unconverted methacrolein and for introducing fresh methacrolein into the oxidation stage.

SUMMARY OF THE INVENTION

The present invention, then, provides a process for preparing methacrylic acid by gas phase oxidation of methacrolein or isobutyraldehyde with an oxygen- and steam-containing gas mixture over a molybdenum- and phosphorus-containing catalyst at from 250° to 400° C. where the hot reaction gas from the oxidation reactor is cooled down to below 100° C., is passed, for absorption of the methacrylic acid formed, through an absorption column (1) operated with water at below 100° C., and, after being replenished with a fresh quantity of methacrolein or isobutyraldehyde and oxygen corresponding to the quantity of these substances consumed, is partly recycled into the oxidation reactor. The process comprises feeding a quantity of methacrolein or isobutyraldehyde equal to the quantity of methacrolein or isobutyraldehyde consumed in the reaction, in liquid form together with a polymerization inhibitor, into the reactor gas in the lower two-thirds of absorption column (1) and upstream of the feed point for the fresh methacrolein or isobutyraldehyde or downstream of absorption column (1) splitting off the reactor offgas a side stream which is washed in a wash column (2) operated with water at from 0° to <10° C. to remove unconverted methacrolein or isobutyraldehyde which is fed as an aqueous solution to the top of absorption column (1). In a preferred embodiment of the process, the hot offgas from the oxidation reactor is initially cooled indirectly to from 220° to 260° C. and then cooled down rapidly in a quench tube equipped with spray nozzles to from more than 70° to about 80° C. with the aqueous methacrylic acid solution obtained. Suitable polymerization inhibitors are for example hydroquinone, hydroquinone monomethyl ether, benzoquinone and combinations thereof with, for example, diphenylamine.

The effect of the measures according to the invention is not only to virtually completely suppress in the cooling zones the deposition of polymer and the formation of aerosols containing methacrylic acid and high boilers but also to substantially prevent any temporary or irreversible reduction in the performance of the oxidation catalyst due to high-boiling or catalyst-poisoning lower-boiling impurities in the fresh methacrolein or isobutyraldehyde.

The novel process for preparing methacrylic acid by gas phase oxidation of methacrolein or isobutyraldehyde is notable for the low level of losses in the removal of methacrylic acid and the recovery and recycling of unconverted methacrolein and or isobutyraldehyde.

BRIEF DESCRIPTION OF THE FIGURES

In what follows, the novel process will be elucidated by reference to FIGS. 1 and 2.

DETAILED DESCRIPTION OF THE PREFERRED EMBODIMENTS

Figure 1:
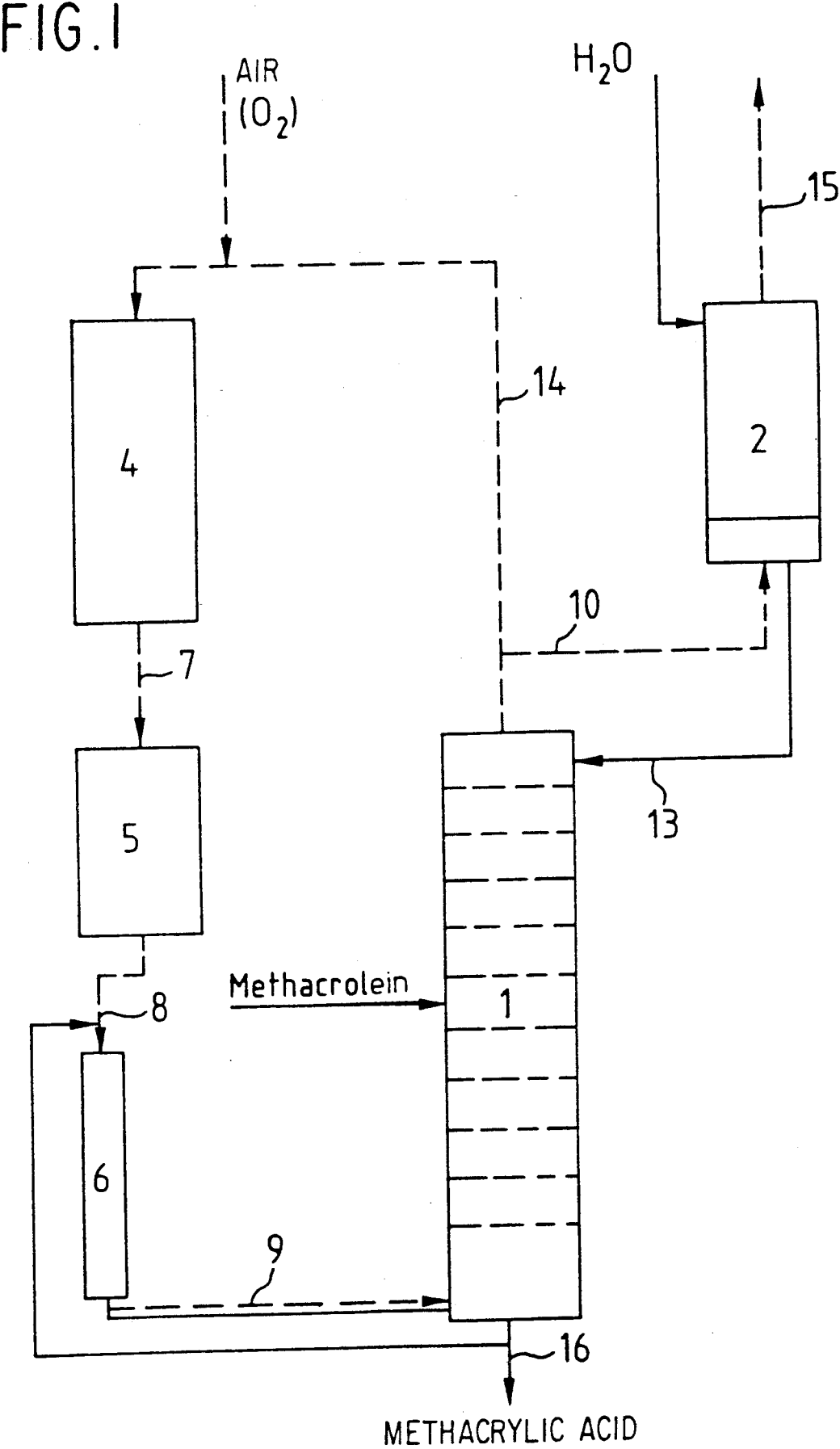

In a preferred embodiment, the hot reaction gas (7) which generally emerges from the oxidation reactor (4) at from 300° to 340° C. is initially cooled down from 220° to 260° C., preferably to from 230° to 250° C., in a heat exchanger (5). This heat exchanger can comprise any conventional heat exchanger, for example a tubular heat exchanger, which is operated with pressurized water or other cooling media, whose specific heat-exchanging area is advantageously more than 200 $m^2/m^3$, and which is joined directly, i.e. without major uncooled intermediate space, to the bottom tube plate of the oxidation reactor in order to prevent non-catalytic afterburning of the methacrolein-containing reaction gas. Tube bundle reactors for the catalytic conversion of methacrolein where a part of the tube at the gas outlet which is packed with inert packing has a separate coolant cycle are likewise suitable. The precooled reaction gas (8) is subsequently rapidly cooled down to from more than 70° to about 80° C. in a quench tube (6) equipped with spray nozzles with the aqueous methacrylic acid solution obtained before entry into the absorption column (1) for the methacrylic acid. We have found, surprisingly, that if a temperature limit of from more than 70° to 80° C. is maintained as part of the process according to the invention not only the precipitation of the polymer but also the formation of aerosols is suppressed virtually completely. And, contrary to GB Patent. 2,116,963, it is not necessary to carry out the quenching process in a cooling tower equipped with sieve plates without downcomers and followed on the downstream side by a Venturi washer. It is true that it can be advantageous for the quenching tube to be used to take the form of a Venturi tube in order to intensify the contact between the gas phase and the liquid phase containing polymerization inhibitors, but this measure is not essential to the invention because it does not prevent aerosol formation if the quenching temperature is markedly less than 70° C. The quenched reaction gas (9) is washed in the absorber (1) at from more than 70° to about 80° C. and under pressures from about 1.1 to 2 bar to remove the methacrylic acid together with medium- and high-boiling byproducts, such as acetic acid, propionic acid, acrylic acid, maleic acid, fumaric acid, citraconic acid, formaldehyde and formic acid. The construction of absorber (1) is not essential to the invention.

Suitable absorbers include, for example, columns packed with, e.g., Raschig rings, and also sieve or perforated plate columns with or without downcomers. The absorbing medium used is water which, together with polymerization inhibitors, is initially introduced at the top of absorber (2) in order to wash unconverted methacrolein out of branch streams (10) or (11) and (12) of the reaction gas; the methacrolein-containing offliquor (13) from absorber (2) is pumped in at the top or onto the upper plates of methacrylic absorber (1), where the dissolved methacrolein is desorbed and recycled together with the steam-saturated offgas from absorber (1) into oxidation reactor (4) as cycle gas (14). An essential feature of the invention is the introduction of fresh methacrolein into absorption column (1). We have found, surprisingly, that the performance of existing catalysts for methacrolein oxidation is not independent of where and in which form the methacrolein is introduced into the oxidation reactor. This is true in particular of the methacrolein prepared by condensation of propanal with formaldehyde in the presence of secondary amines or aminals. If the methacrolein was introduced into the cycle gas by evaporation downstream of absorber (1) for methacrylic acid, the catalyst performance was poorer than when the methacrolein was introduced as a liquid or as an aqueous solution, ie. in liquid form, into the bottom two-thirds of absorption column (1).

The branching of a side stream (10) or (11) off the reaction gas is necessary to channel out the carbon oxides formed together with unconsumed oxygen and uncondensable inert gases. The branch can go off to a catalytic or thermal incinerator. For the point where the side stream is branched off there is a choice between downstream of methacrylic acid absorber (1) and below the feed point for fresh methacrolein. If the latter, the branch stream is first passed into absorber (3) to wash out the methacrylic acid with water at below 70° C. before the stream is passed into absorber (2). An advantage of this preferred embodiment is for example a lowering in the operating pressure.

The from 10 to 20% strength aqueous methacrylic acid solution (16) withdrawn from the base of absorbers (1) and (3) contains in generally only small amounts of methacrolein of not more than 3% by weight, based on the methacrylic acid present in the solution. This residual amount of methacrolein can for example be driven off with air or inert gases and be mixed in with the cycle gas.

Cycle gas recycled into the oxidation reactor contains aside from the requisite amount of methacrolein and steam very low levels of low boilers, such as acetaldehyde, acetone, acrolein and propionaldehyde. On admixture of an amount of oxygen, in the form of pure oxygen or air, identical to the amount of oxygen consumed, the synthesis gas usually has the composition of from 3 to 7% by volume of methacrolein, from 5 to 10% by volume of $O_2$, from 15 to 30% by volume of $H_2O$, and less than 0.1% by volume of low boilers, the remainder comprising inert gases, such as $N_2$, CO and $CO_2$.

The conversion of methacrolein is in general carried out at from 250° to 400° C. under space velocities of from 500 to 2000 $h^{-1}$ and pressures of from 1 to 3 bar. It has proved to be advantageous to select the space velocity and the reaction temperature to be such that the methacrolein conversion in a single pass is from 50 to 80 mol %, preferably from 55 to 75 mol %. The catalysts, in addition to Mo and P, generally contain still other components and have the structure of heteropolyacids and salts thereof. Particularly suitable catalysts contain Mo, P, V or Nb, one or more alkali metals and/or alkaline earth metals, one or more elements from the group consisting of Cu, Ag, Au, Fe, Co, Ni, Mn, Cr, Zr, Ge, Se, Te, Tl, In, Ga, Zn, Cd, Hg, rare earths, Rh, Re, Sb, U, B, As and/or W and an inert carrier. Particularly high effectiveness under the operating conditions of the process according to the invention is shown by catalysts of a composition represented by the general formula $$Mo_{12} P_a V_b Nb_c Cs_d Cu_e M_{1f} M_{2g} M_{3h} M_{4i}$$

where
  $M_1$ is K, Rb and/or TL,
  $M_2$ is Be, Mg, Ca, Sr and/or Ba,
  $M_3$ is Fe, Ni, Co, Ag, Zn, a rare earth, Re, Mn, Ta, Ge, Si, Te, Se, In, W, Rh and/or Sb,
  $M_4$ is As and/or B,
  a is from 0.1 to 4,
  b is from 0 to 4, preferably from 0.05 to 2,
  c is from 0 to 4,
  b+c is from 0.05 to 4,
  d is from 0 to 3, preferably from 0.5 to 2,
  e is from 0 to 2, preferably from 0.05 to 1,
  f is from 0 to 3,
  g is from 0 to 3,
  d+f is from 0.05 to 3, preferably from 0.5 to 3,
  h is from 0 to 2,
  e+h is from 0.05 to 2, preferably 0.05 to 1,
  i is from 0 to 2,
  k is the number of oxygen atoms required for the formal saturation of the valencies of the other elements.

Catalysts of this type are comparatively impervious to impurities in the methacrolein and produce fewer high-boiling aldehydes such as furfural which are difficult to separate off in the extractive and distillative purification of methacrylic acid.

The advantages of the process according to the invention over the existing processes are further illustrated by the following Example:

EXAMPLE

In an apparatus conforming to the sketched arrangement of FIG. 1, methacrolein was oxidized in the gas phase over a catalyst of the formal composition

$$Mo_{12} P_{1.9} V_1 Cs_{1.9} Cu_{0.5} Rh_{0.008} O_x$$

to give methacrylic acid. The test conditions are summarized in Table 1.

TABLE 1

| | |
|---|---|
| Reactor (4) | 3 m in tube length, 26 mm in diameter |
| Pressure at inlet to reactor (4) | 1.35 bar |
| Reaction temperature | 315° C. |
| Catalyst quantity | 1 l (6 × 6 × 2 mm hollow cylinders) |
| Fresh air rate | 258 l(S.T.P.)/hour |
| Liquid methacrolein supply rate | 118 g/hour |
| Cycle gas rate | 900 l(S.T.P.)/hour |
| Wash water into methacrolein absorber (2) | 1104 g/hour |
| Exit temperature of reaction gas from heat exchanger (5) | 240° C. |
| Gas temperature at outlet of quench tube (6) | 80° C. |
| Top of column temperature of methacrylic acid absorber (1) | 72° C. |
| Temperature of methacrolein absorber (2) | 4° C. |

The methacrolein introduced in liquid form (undiluted) into a center portion of methacrylic acid absorber contained 96.3% by weight of methacrolein, 2.1% by weight of water, 1.1% by weight of methanol, 0.2% by weight of propanal, 0.22% by weight of high boilers, such as dimeric methacrolein, and also about 150 ppm N-containing compounds. From the analysis of the offgas stream from the methacrolein absorber (15) and the aqueous methacrylic acid solution takeoff (16) it was possible to calculate a conversion of 98.5 mol % and a methacrylic acid yield of 83.4 mol %, both values based on fresh methacrolein. The single pass conversion was 59.9 mol %, which virtually stayed the same over a test period of 4 weeks. No aerosol formation was observed. The pressure drop in the columns and the oxidation reactor remained constant over the test period. Even replacing the perforated plate column by a column packed with Raschig rings did not give rise to any solid deposits in methacrylic acid absorber (1).

COMPARISON A

Example 1 was repeated, except that the methacrolein was not metered in liquid form into absorption column (1) but was introduced via an evaporator into the cycle gas in gas form. Within 3 days the single pass conversion dropped from 60 mol % to below 50 mol % together with a steady increase in the methacrolein concentration in cycle gas (14), branch stream 10 and the bottom product solution from methacrolein absorber (2).

COMPARISON B

In a further run, the quench temperature was reduced from 80° C. to 45° C. This measure brought about visible misting in the offgas stream from the quench tube. The emerging aerosol was passed through the methacrylic acid absorber and was returned into the reactor together with the cycle gas. The pressure drop across a filter upstream of the reactor increased by 0.5 bar in the course of 10 days. The run was then discontinued.

COMPARISON C

In a further run, the coolant temperature of heat exchanger (5) was lowered to such an extent that the reaction gas was cooled down to a temperature of 200° C. Within a week the pressure drop across the heat exchanger then increased to such an extent that the run had to be discontinued. Subsequent inspection of heat exchanger tube 2 showed that the inner surface was coated with a solid blackish brown mass.

We claim:

1. A process for preparing methacrylic acid by gas phase oxidation of methacrolein or isobutyraldehyde with an oxygen-and steam-containing gas mixture over a molybdenum- and phosphorus-containing catalyst at from 250° to 400° C. in which hot reaction gases from the oxidation reaction are cooled down to below 100° C., passed, for absorption of the methacrylic acid formed, through an absorber operated with water at below 100° C., and, after being replenished with a fresh amount of methacrolein or isobutyraldehyde and oxygen corresponding to the amount of these substances consumed in said oxidation reaction, said gases are partly recycled into the oxidation reaction, which process further comprises feeding an amount of fresh methacrolein or isobutyraldehyde equal to the amount of methacrolein or isobutyraldehyde consumed in said oxidation reaction, in liquid form, together with a polymerization inhibitor, into said reaction gas in the lower two-thirds of said absorber, and either (i) upstream of the feed point for said fresh methacrolein or isobutyraldehyde or (ii) downstream of said absorber, splitting off the reaction offgas a side stream which is washed in a wash column operated with water having a temperature of from 0° to <10° C. to remove unconverted methacrolein or isobutyraldehyde which is fed as an aqueous solution to the top of said absorber.

2. The process of claim 1, wherein hot reaction gas from the oxidation reaction is initially cooled down indirectly to a temperature of from 220° to 260° C. and then cooled down rapidly in a quench tube equipped with spray nozzles to a temperature of from more than 70° to about 80° C., with the methacrylic acid solution obtained.

3. The process of claim 1, wherein a side stream of said reaction gas is branched off upstream of the feed point of said fresh methacrolein or isobutyraldehyde and first passed into an absorber to wash out the methacrylic acid with water and then into a further absorber for separating off remaining methacrolein.

4. The process of claim 1, carried out with methacrolein prepared by condensation of propanal with formaldehyde in the presence of a secondary amine or aminal.

5. The process of claim 1, comprising splitting off said reaction offgas upstream of the feed point for said fresh methacrolein or isobutyraldehyde.

6. The process of claim 1, comprising splitting off said reaction offgas downstream of said absorption column.

* * * * *